(12) United States Patent
Wilson et al.

(10) Patent No.: US 10,273,367 B2
(45) Date of Patent: Apr. 30, 2019

(54) BIOCIDAL PROTECTIVE FORMULATIONS

(71) Applicant: Autonomic Materials, Inc., Champaign, IL (US)

(72) Inventors: Gerald O. Wilson, Savoy, IL (US); Byron R. Ebbert, Mansfield, IL (US)

(73) Assignee: Autonomic Materials, Inc., Champaign, IL (US)

( * ) Notice: Subject to any disclaimer, the term of this patent is extended or adjusted under 35 U.S.C. 154(b) by 155 days.

(21) Appl. No.: 15/671,271

(22) Filed: Aug. 8, 2017

(65) Prior Publication Data

US 2018/0037749 A1     Feb. 8, 2018

Related U.S. Application Data

(60) Provisional application No. 62/372,157, filed on Aug. 8, 2016.

(51) Int. Cl.
| | |
|---|---|
| *A01N 25/28* | (2006.01) |
| *C08L 33/12* | (2006.01) |
| *C09D 5/14* | (2006.01) |
| *C09D 7/63* | (2018.01) |
| *A01N 43/80* | (2006.01) |
| *B01J 13/14* | (2006.01) |

(52) U.S. Cl.
CPC ............... *C09D 5/14* (2013.01); *A01N 25/28* (2013.01); *A01N 43/80* (2013.01); *B01J 13/14* (2013.01); *C09D 7/63* (2018.01)

(58) Field of Classification Search
CPC ......... A01N 25/28; A01N 43/80; B01J 13/14; C09D 5/14; C09D 7/63
See application file for complete search history.

(56) References Cited

U.S. PATENT DOCUMENTS

| | | |
|---|---|---|
| 2007/0215000 A1 | 9/2007 | Reybuck et al. |
| 2009/0186058 A1 | 7/2009 | Hart et al. |
| 2010/0099793 A1 | 4/2010 | Wunder |
| 2011/0008610 A1* | 1/2011 | Hayward ............... A01N 25/28 428/323 |
| 2012/0071324 A1* | 3/2012 | Uhr ......................... A01N 25/10 504/158 |
| 2014/0141263 A1* | 5/2014 | Jones ................... C09D 5/1625 428/447 |
| 2014/0341962 A1 | 11/2014 | Ashmore et al. |
| 2014/0371362 A1 | 12/2014 | Wilson |
| 2015/0111987 A1* | 4/2015 | Wilson ................... B29C 73/22 523/209 |
| 2015/0223450 A1* | 8/2015 | Ashmore ............... A01N 25/10 424/501 |
| 2015/0259543 A1* | 9/2015 | Ashmore ................. C09D 5/16 428/414 |
| 2016/0346753 A1* | 12/2016 | Shukla ................... B01J 13/185 |
| 2017/0100902 A1* | 4/2017 | Asmatulu ............... C08L 63/00 |
| 2017/0158886 A1* | 6/2017 | Odarczenko ......... C09D 163/00 |

* cited by examiner

*Primary Examiner* — Irina S Zemel

(74) *Attorney, Agent, or Firm* — Schwabe, Williamson & Wyatt, P.C.

(57) ABSTRACT

Disclosed are biocidal self-healing protective materials, including coatings, stains, sealants, and adhesives. The biocidal protective materials may include a first microcapsule that includes a hydrophobic film-forming agent and a hydrophobic biocidal agent. Upon rupture of the first microcapsule, the hydrophobic film-forming agent may form a polymerized film that includes the hydrophobic biocidal agent. The biocidal protective materials may include a second microcapsule that may include a curing agent. Upon rupture of the first and second microcapsules, the curing agent may cause the hydrophobic film-forming agent to form a polymerized film that includes the hydrophobic biocidal agent. Also disclosed are protective materials that include a polymeric material matrix and the first and/or second microcapsules, as well as methods of increasing the biocidal activity of a protective material and methods of increasing a biocidal activity of a porous substrate.

34 Claims, 7 Drawing Sheets

Encapsulated Biocidal Formulation

Protective Material Matrix

Polymerized Hydrophobic Film-Forming Agent Localizing Hydrophobic Biocidal Agent in Place Substrate Susceptible to Bio Matter Growth

Figure 3

BIOCIDAL PROTECTIVE FORMULATIONS

CROSS REFERENCE TO RELATED APPLICATION

The present application claims priority to U.S. Provisional Application No. 62/372,157, which was filed on Aug. 8, 2016, and titled "BIOCIDAL PROTECTIVE FORMULATIONS," and which is hereby incorporated by reference herein.

TECHNICAL FIELD

Embodiments herein relate to self-healing materials, particularly biocidal self-healing protective materials, including coatings, stains, sealants, and adhesives.

BACKGROUND

Many porous substrates, such as wood or concrete, are susceptible to damage from biomatter such as bacteria, fungi such as mold and mildew, and algae. Many protective coatings applied to such substrates may fail mechanically over time. For example, protective coatings may crack from the stress of thermal cycling (e.g., from weather conditions), or they may be damaged by impact or may sustain scratches from use. These damage sites quickly become areas where the underlying substrate is exposed, and biomatter can begin to grow, causing further damage to the protective coating and/or underlying substrate.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

FIG. 3 is a schematic illustration showing a substrate protected by a coating or stain containing the microcapsules of FIG. 2, wherein the hydrophobic biocidal agent and the hydrophobic film-forming agent are released in the site of damage, in accordance with various embodiments;

DETAILED DESCRIPTION OF EMBODIMENTS OF THE INVENTION

Figure 1:
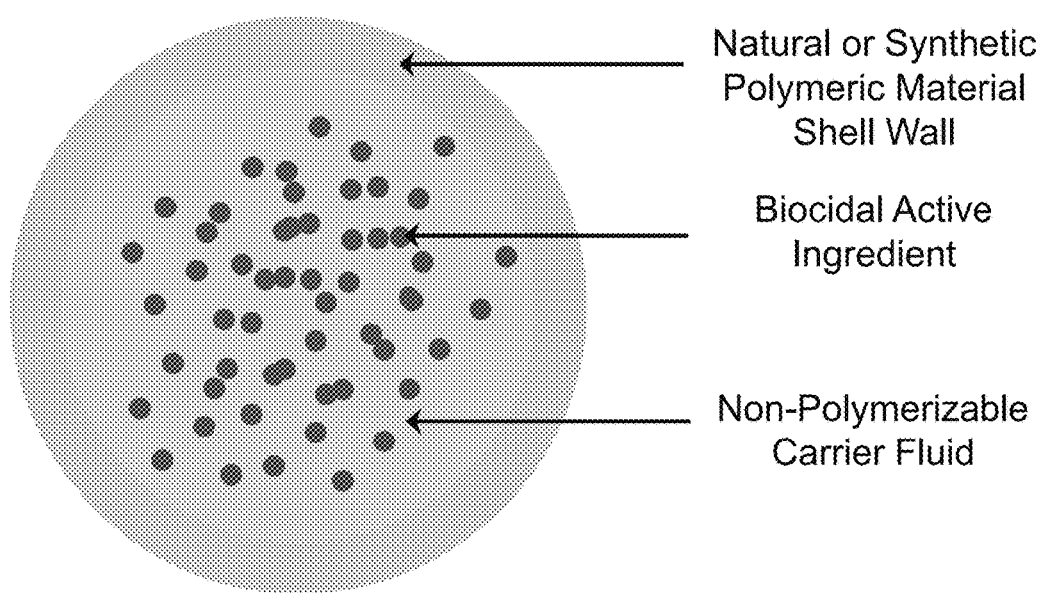
FIG. 1 is a schematic illustration showing a common prior art approach to the encapsulation of biocidal agents, wherein the release of the biocidal agent is controlled to lengthen the period of biocidal efficacy, in accordance with various embodiments.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

Disclosed in various embodiments are biocidal microcapsule formulations for protective materials, such as coatings, stains, sealants, and adhesives. In various embodiments, the disclosed biocidal microcapsule formulations may release and retain one or more biocidal agents at the site of damage when damage occurs to the protective material, allowing the biocidal agent(s) to prevent the growth of biomatter (e.g., bacteria, fungi such as mold and mildew, or algae) in or on the exposed substrate. In various embodiments, the disclosed biocidal microcapsule formulations may include microencapsulated liquid formulations that include one or more hydrophobic film-forming agents and one or more hydrophobic biocidal agents.

In various embodiments, the biocidal microcapsule formulations may be mixed into a protective material, such as a coating, stain, sealant, or adhesive, prior to application of the protective material to a substrate. Subsequently, in the event of damage to the protective material, the microcapsules may rupture, releasing the hydrophobic biocidal agent(s) and the hydrophobic film-forming agent(s) into the site of damage. In various embodiments, the hydrophobic film forming agent(s) then may form a solidified (e.g., polymerized) film (such as a polymerized resin) that contains the hydrophobic biocidal agent(s) and serves as an anchoring agent for the hydrophobic biocidal agent(s). Thus, in various embodiments, the hydrophobic biocidal agent(s) may be held in place in the site of damage by the polymerized film. Also disclosed in various embodiments are methods of using microcapsules containing one or more hydrophobic biocidal agents and one or more hydrophobic film-forming agents to maintain the biocidal activity of a protective material, such as a coating, stain, sealant, or adhesive, after it has been damaged.

As used herein, the term "protective material" refers to any polymeric material applied on or between substrates for the purpose of protecting the substrate or joining and protecting two substrates in contact with each other. In specific, non-limiting examples, a protective material applied on a substrate may take the form of a coating or stain, while a protective material applied between substrates may take the form of an adhesive or a sealant.

As used herein, the term "hydrophobic biocidal agent" refers to a hydrophobic chemical substance that can destroy, deter, render harmless, retard the growth of, or otherwise exert a controlling effect on any harmful organism, such as bacteria, fungi, or algae. In various embodiments, hydrophobic biocidal agents for use in the disclosed formulations include any hydrophobic liquid that is miscible with hydrophobic non-polar and/or polar aprotic solvents. In various embodiments, the biocidal agent alternately may be a solid that is soluble in a hydrophobic solvent or that may form a stable suspension in a hydrophobic solvent. One specific, non-limiting example of a hydrophobic biocidal agent for use in the disclosed formulations and methods is 4,5-dichloro-2-n-octyl-4-isothiazolin-3-one (DCOIT). Another specific, non-limiting example of a hydrophobic biocidal agent for use in the disclosed formulations is benzisothiazolin-3-one (BIT). Although both of these specific, non-limiting examples are isothiazolinones, this disclosure is not limited to hydrophobic biocidal agents that are isothiazolinones, and one of skill in the art will appreciated that other hydrophobic biocidal agents may be substituted, so long as they are effective against the desired organisms and compatible with the other components of the microcapsules and microcapsule contents.

As used herein, the term "hydrophobic film-forming agent" refers to any hydrophobic material that solidifies (e.g., polymerizes) to form a cohesive, continuous layer in a damage site in a protective material. In various embodiments, the solidification or polymerization of the hydrophobic film-forming agent may be initiated by any of a number of physical and chemical processes, including but not limited to solvent evaporation and any of various cross-linking reactions. In various embodiments, cross-linking of the film-forming agent in the microencapsulated biocidal formulation may proceed via oxygen initiation, or may be initiated by a cross-linking agent present either in the protective material or released from a separate capsule. Specific, non-limiting examples of hydrophobic film-forming agents for use in the formulations and methods disclosed herein include thermoplastic polymers dissolved in appropriate diluents, and monomers or resins including but not limited to alkyds, epoxies, siloxanes, silanes, polyesters, vinyl esters, silicones, isocyanates, polyacrylates, polyurethanes, polyureas, and acrylates.

As used herein, the term "microcapsule" refers to a small sphere with a uniform wall around it. The material inside the microcapsule is referred to as the core, internal phase, or fill, whereas the wall is referred to as a shell, coating, or membrane. Most microcapsules have diameters of from a few microns to about 100 microns. Specific, non-limiting examples of shell wall materials for use in the disclosed formulations and methods include, but are not limited to poly(oxymethylene urea), poly(oxymethylene melamine), polyurethane, polyurea, polyacrylate, gelatin, polydimethylsiloxane, various thermoplastic polymers or monomers, and resins, such as alkyds, epoxies, siloxanes, silanes, isocyanates and acrylates.

In various embodiments, a combination of compatible film-forming agent(s) and biocidal agent(s) may reside within the microcapsules in a quiescent form within the protective material prior to a damage event. In various embodiments, when damage occurs to the protective material (e.g., from abrasion, cracking, thermal cycling, etc.), the contents of the microcapsules may be released into the site of damage, whereupon solidification and/or polymerization of the film-forming agent(s) causes the film to polymerize, thus retaining the biocidal agent(s) in place at the site of damage. In various embodiments, the biocidal activity is thereby maintained where it is needed at the site of damage. In various embodiments, in order to be effective, in addition to being compatible with the biocidal agent(s), the film forming agent(s) may have excellent adhesion to the target substrate. In various embodiments, biocidal activity may be maintained in the site of damage for much longer periods of time when the biocidal agent(s) are contained in a film that is well adhered to the substrate. In specific, non-limiting embodiments, the substrate may be wood, concrete, ceramic, or plastic.

In various embodiments, for facile encapsulation via common oil-in-water emulsion-based microencapsulation procedures, the core formulation (e.g., the formulation that ends up within the microcapsules) may be hydrophobic. As such, in various embodiments, the film-forming agents, solvents incorporated for viscosity modification, and biocidal agents may together form a homogenous and hydrophobic liquid core. Specific, non-limiting examples of film-forming agents that meet these criteria include hydrophobic alkyd, epoxy, polyester, vinyl ester, silicone, polyacrylate, polyurethane and polyurea resins. In various embodiments, any hydrophobic solvent may be included the core formulation, so long as it is compatible with the other components of the core formulation. In various embodiments, the biocidal agent may be any hydrophobic liquid that is miscible with hydrophobic non-polar and/or polar aprotic solvents. In various embodiments, the biocidal agent alternately may be a solid that is soluble in a hydrophobic solvent or that may form a stable suspension in a hydrophobic solvent. Specific, non-limiting examples of biocidal agents that meet these criteria include isothiazolinone derivatives such as DCOIT and benzisothiazolin-3-one (BIT).

In some conventional protective materials, a biocidal agent might be added to the material in order to prevent the growth of biomatter on the coated substrate. However, such biocidal agents typically are mixed directly into the protective material. When a biocidal agent is mixed directly into a protective material, it may leach away over time due to environmental factors, such as rain or immersion of the coated substrate in water.

In other conventional approaches, microencapsulation may be used to preserve the activity of a biocidal agent in a protective material by allowing for controlled release over time, for example from biodegradable microcapsules formed from cellulose, chitin, lignin, or other biodegradable substances, or by water facilitating leaching of the biocide out from the capsules. In both instances, the eventual leaching of the biocidal agent is slowed, extending the biocidal activity of the formulation. However, upon damage, materials incorporating microencapsulated biocides will exhibit loss of biocidal activity at the site of damage, either because the microcapsules containing the biocidal agent were not designed to rupture and release their contents when they are damaged, or because upon release of the biocidal agent into the site of damage, without a film to keep it anchored in place, it simply washes away over time. By contrast, the microcapsules of the present disclosure are designed to rupture when the protective material is damaged, and the inclusion of one or more hydrophobic biocidal agents and one or more hydrophobic film-forming agents in the microcapsules allows the hydrophobic biocidal agent(s) to be sequestered and anchored at the site of damage. One of skill in the art would appreciate that microcapsules designed to release their contents as a result of rupturing would reflect a different set of chemical and/or mechanical properties relative to those designed only to facilitate controlled and slow release of their contents. These properties are discussed in greater detail below.

Thus, in various embodiments, the disclosed microencapsulated formulations prevent the one or more hydrophobic biocidal agents from leaching out of the protective coating when the coating is intact, thereby providing a long-lasting biocidal formulation. Furthermore, when damage to the protective coating occurs, the microcapsules rupture and release a composition that includes both the hydrophobic biocidal agent and the hydrophobic film-forming agent into the site of damage. Biocidal activity is thereby activated in the site of damage, and the hydrophobic film-forming agent polymerizes and prevents the biocidal activity from dissipating from the site of damage. More specifically, the hydrophobic film-forming agent solidifies and/or polymerizes to form a solidified and/or polymerized film that localizes the hydrophobic biocidal agent at the site of damage, thereby promoting the longevity of biocidal activity at the site of damage. To accomplish both functions, in various embodiments, the microcapsule shell wall may be robust enough to contain core formulation, but may exhibit mechanical properties that allow the capsules to rupture when damage to the protective coating occurs. In various embodiments, rupturable microcapsules for use in the disclosed formulations may have a core material that is 60% or greater of the total mass of the capsule, the thickness of the shell wall may be 2 microns or less, and the contribution of the average shell wall thickness to the average capsule diameter may be no more than about 20%.

FIG. 1 is a schematic illustration showing a common prior art approach to the microencapsulation of biocidal agents, wherein the release of the biocidal agent is controlled to lengthen the period of biocidal efficacy, in accordance with various embodiments. As described above, some prior art protective material formulations have incorporated biocidal agents, including microencapsulated biocidal agents. In these microencapsulated formulations, the biocidal agents generally are microencapsulated in biodegradable or generally degradable materials in order to control the release of the biocidal agent over time, thereby extending the efficacy of the biocidal agent relative to a non-microencapsulated biocidal agent. In most examples, the biocidal agent is dissolved or dispersed in a carrier fluid, followed by encapsulation in a polymeric shell wall, as illustrated in FIG. 1. Upon incorporation into the protective material, the biocide is either gradually released into the material by escaping through the shell wall or via gradual degradation of the shell wall.

Figure 2:
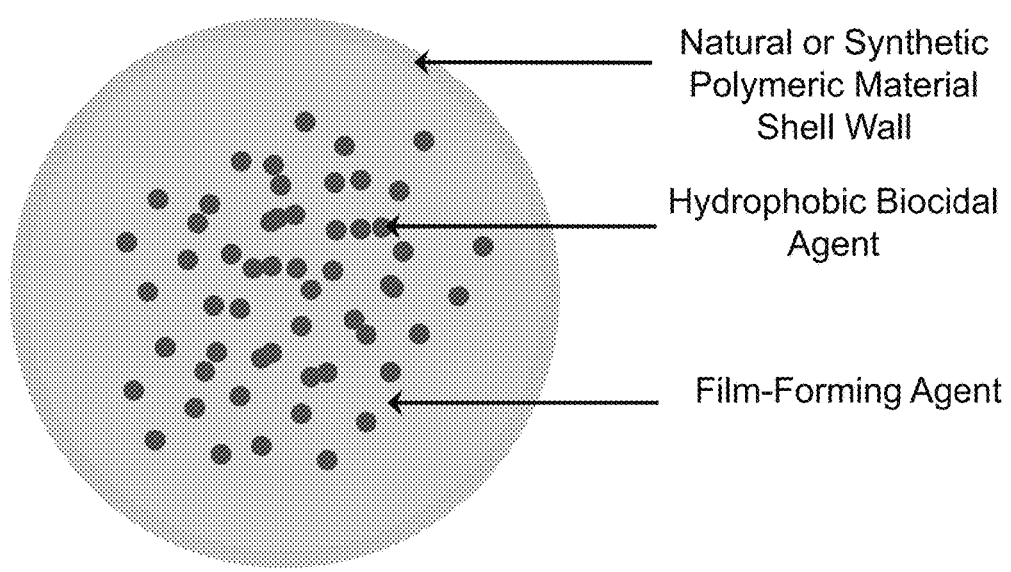
FIG. 2 is a schematic illustration showing a new biocidal system as disclosed herein, wherein a hydrophobic biocidal agent is microencapsulated in a microcapsule with a hydrophobic film-forming agent, and wherein the microcapsule has a shell wall that ruptures when the protective material (e.g., the coating, stain, sealant or adhesive, generally referred to as the matrix) in which the microcapsule is incorporated is damaged, in accordance with various embodiments.

A limitation of such prior art formulations is that even when biocides are incorporated into the protective material, damage to the protective material creates sites in which bacteria, fungi such as mold and mildew, algae, and other biomatter may begin to grow. This is particularly true because the biocide is neither released nor retained at the site of damage. By contrast, FIG. 2 is a schematic illustration showing a new biocidal system as disclosed herein, wherein a hydrophobic biocidal agent is microencapsulated in a microcapsule with a hydrophobic film-forming agent, and wherein the microcapsule has a shell wall that ruptures when the protective material (e.g., the coating, stain, sealant, or adhesive, all of which may be referred to herein using the more general term "matrix") in which the microcapsule is incorporated is damaged, in accordance with various embodiments. In the illustrated embodiment, the damage may be due to any of a variety of factors, such as mechanical, thermal, or other stress.

FIG. 3 is a schematic illustration showing a substrate protected by a protective material containing the microcapsules of FIG. 2, wherein the hydrophobic biocidal agent(s) and hydrophobic film-forming agent(s) are released in the site of damage, in accordance with various embodiments. In various embodiments, the biocidal, film-forming microcapsules may be mixed into a protective material, such as a coating, matrix, sealant, or adhesive, such that damage to the protective material causes release of the hydrophobic biocidal agent and hydrophobic film-forming agent into the site of damage. In various embodiments, once in the site of damage, the hydrophobic film-forming agent solidifies, polymerizes, and/or hardens to form a film, which localizes and immobilizes the hydrophobic biocidal agent at the site of damage, staving off the onset of the growth of damaging biomatter common to the environment of the protected substrate.

Thus, in various embodiments, the disclosed biocidal formulations may be embodied as hydrophobic formulations containing a hydrophobic film-forming carrier and a hydrophobic biocide encapsulated by a polymeric shell wall. In some embodiments, the shell wall may be selected from a set of polymeric materials including but not limited to poly (oxymethylene urea), poly(oxymethylene melamine), polyurethane, polyurea, polyacrylate, gelatin, polydimethylsiloxane and various thermoplastic polymers.

Figure 4:
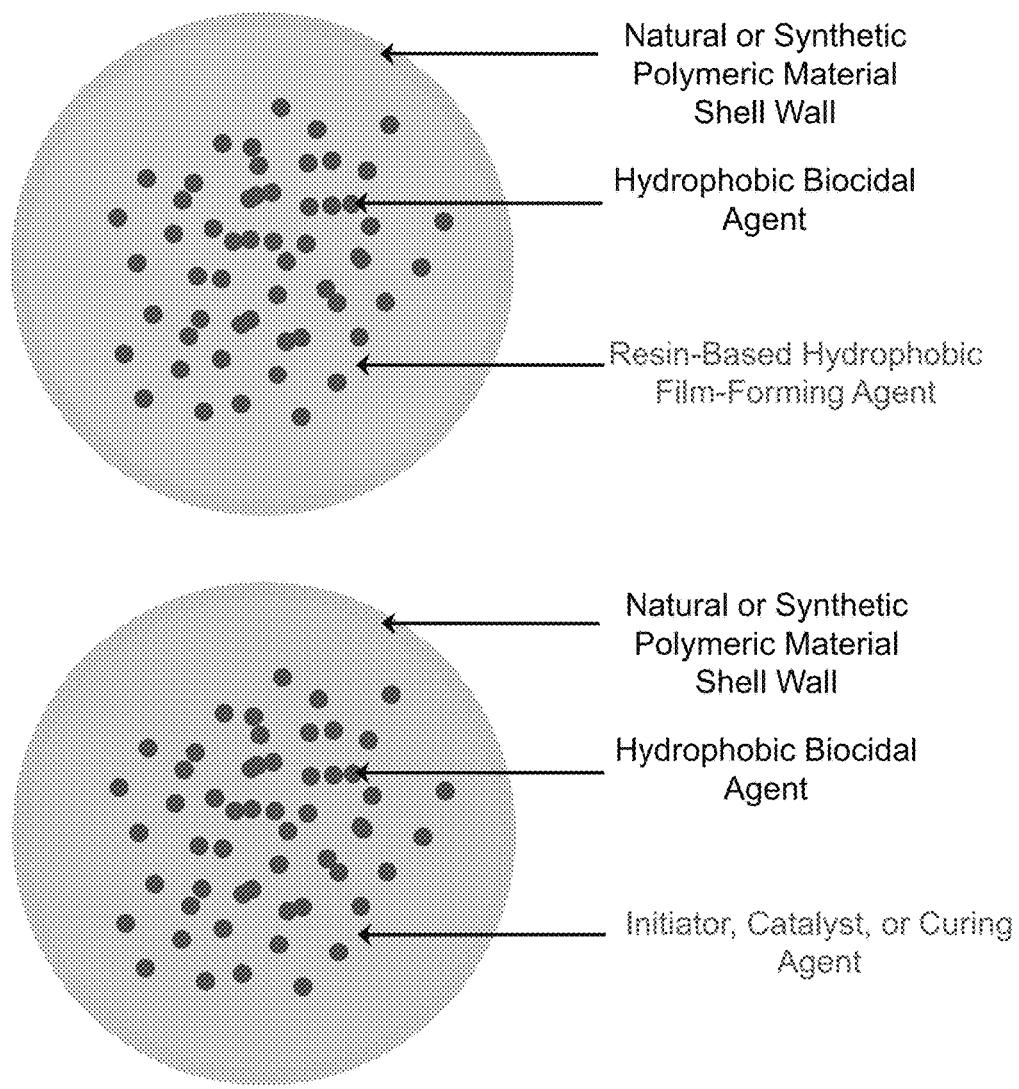
FIG. 4 is a schematic illustration showing a dual-microcapsule biocidal system, wherein the hydrophobic biocidal agent is microencapsulated with a complementary hydrophobic film-forming agent in a first microcapsule, and with a complementary curing agent in a second microcapsule, in accordance with various embodiments.

FIG. 4 is a schematic illustration showing a dual-microcapsule biocidal system, wherein the hydrophobic biocidal agent(s) are microencapsulated with a complementary hydrophobic film-forming agent in a first microcapsule, and with a complementary curing agent in a second microcapsule, in accordance with various embodiments. Although in the illustrated embodiment, the hydrophobic biocidal agent is shown as being present on both the first and second microcapsules, in some embodiments, the hydrophobic biocidal agent may be present in only the first microcapsule, and the second microcapsule may contain only a curing agent. In various embodiments, the solidification and/or polymerization of the hydrophobic film forming agent may be initiated by any of a number of physical and/or chemical processes, including but not limited to solvent evaporation and various cross-linking reactions. As illustrated in FIG. 4, in some embodiments, cross-linking of the hydrophobic film-forming agent in the encapsulated biocidal formulation may proceed via initiation by a cross-linking agent (e.g., a curing agent) present either in the protective material matrix (also referred to herein as a "polymeric material matrix") or released from a separate capsule. In the illustrated embodiment, complementary hydrophobic film-forming agent (e.g. resin) and curing agent materials are incorporated into separate microcapsules in the biocidal formulations as carrier fluids for the hydrophobic biocidal agent(s). In various embodiments, both capsule types may be incorporated into the protective material, and damage to the protective material may rupture the microcapsules, releasing the microcapsule contents into the site of damage, where they mix and polymerize to form a film that contains the hydrophobic biocidal agent(s). In some embodiments, the hydrophobic film-forming agent may be a thermoplastic polymer dissolved in an appropriate diluent, a monomer, or a resin, including but not limited to an alkyd, an epoxy, a siloxane, a silane, an isocyanate, or an acrylate.

EXAMPLES

Example 1

Microcapsule Preparation

Microcapsules were created that contained the biocide 4,5-dichloro-2-n-octyl-4-isothiazolin-3-one (DCOIT) and one of the following film formers: 1) poly(methyl methacrylate) (PMMA), 2) a silicone epoxy functionalized alkyd, 3) an epoxy resin, 4) a siloxane or silicone resin. For the epoxy resin, separate microcapsules were also created that included DCOIT and a curing agent, thus forming the second of two components of a two-part epoxy-amine resin system. Similarly, for the siloxane or silicone resin, separate microcapsules were created that included DCOIT and a curing agent thus forming the second of two components of an addition-cured polydimethylsiloxane (PDMS) resin system. In cases where a solvent was used as part of the film-forming formulation, the solvents used included xylenes, butyl acetate, hexyl acetate, and phenyl acetate. Specific examples of several microencapsulated biocidal formulations that were generated are provided in Table 1, below:

TABLE 1

| Example | Hydrophobic Film-Forming Agent | Solvent | Hydrophobic Biocidal Agent |
|---|---|---|---|
| 1 | Functionalized Alkyd (30 wt %) | Xylenes (30 wt %), acetate blend (39.8 wt %) | DCOIT (0.2 wt %) |
| 2 | Epoxy Resin (50 wt %) | Xylenes (49.8 wt %) | DCOIT (0.2 wt %) |
|   | Curing Agent (50 wt %) | Xylenes (49.8 wt %) | DCOIT (0.2 wt %) |
| 3 | PMMA, (100 kD, 10 wt %) | Phenyl Acetate (89.8 wt %) | DCOIT (0.2 wt %) |
| 4 | Silicone Encapsulant, Part A (60 wt %) | Hexyl Acetate (39.8 wt %) | DCOIT (0.2 wt %) |
|   | Silicone Encapsulant, Part B (60 wt %) | Hexyl Acetate (39.8 wt %) | DCOIT (0.2 wt %) |

Example 2

Capsule Synthesis 200 mL of deionized $H_2O$ was measured into a clean 1000 mL beaker, although one of skill in the art will appreciate that the reaction may be scaled up or down as needed. 50 mL of a previously prepared solution of 2.5 wt % poly(ethylene-co-maleic anhydride; EMA) was added to the beaker, and 5 g of urea, 0.5 g NH4Cl, and 0.5 g of resorcinol (previously ground), was added and the pH was measured. The pH was adjusted to 3.5 by adding a 10 wt % solution of NaOH to the mixture drop-wise. The mixer was started in order to stir at the desired rate, and 60 mL of the core material was added.

After adding the core material, the mixture was stirred for about 15-20 minutes, and 12.77 g of formaldehyde was added. A hot plate was set to ramp up from room temperature to 55° C. at a rate of 1° C./min (60° C./h). After the completion of the reaction, the reaction mixture was allowed cool to room temperature before the microcapsules were isolated. The microcapsules were isolated and washed via suction filtration, and wet final forms were prepared by adding a specified amount of water to the microcapsules obtained after filtration (slurries containing between 20% and 40% of capsules and filter cakes containing between 45% and 55% of capsules were prepared). Dried capsule final forms were obtained by spray-drying from a slurry containing between 10 and 20 wt % of capsules.

Example 3

Test Sample Preparation

To demonstrate the performance of the microencapsulated biocidal formulations, Southern yellow pine wood samples treated with various formulations were evaluated over time. An initial comparison was made between a non-microencapsulated biocidal formulation that did not include a hydrophobic film-forming agent and one that did.

A typical approach to protecting wood substrates in exterior environments includes the application of a polymeric barrier in the form of a coating or stain that minimizes the rate of moisture penetration and protects the wood from degradation as a result of UV-radiation. These coatings and stains may include a biocide to control the growth of mold and mildew. Since mold and mildew thrive in moist environments, the barrier property of the wood coating or stain is the first line of defense in mold and mildew control working in concert with whatever biocide is included. As such, the direct application of a biocide alone to a wood substrate is unlikely to provide long term biocidal performance, as the biocide will eventually be washed away. This is particularly true in environments wherein the substrate might experience rainfall, is immersed in water, or is otherwise frequently in contact with water. Similarly, for longer-term biocidal activity in a damaged site after damage of the protective material matrix (e.g., the polymeric material matrix, which may include a coating, stain, sealant, adhesive, etc.), the biocidal formulation likely will perform better if it includes a hydrophobic film-forming agent.

Figure 5A:
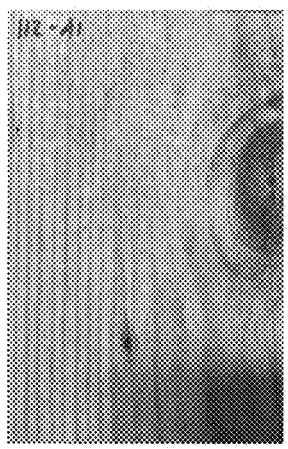
FIGS. 5A-5C show the results of treated Southern yellow pine samples after exterior exposure for 2,750 hours, in accordance with various embodiments.
Figure 5B:
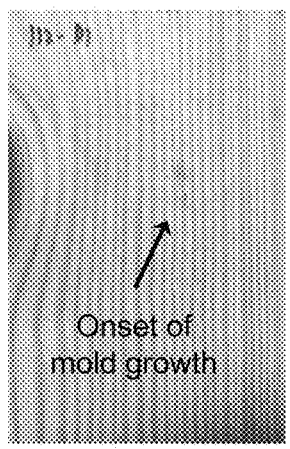
Figure 5C:
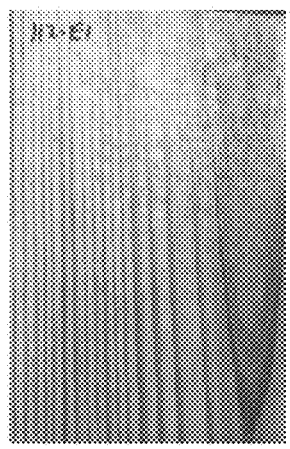

To demonstrate this, Southern yellow pine samples were treated with two different formulations described in Table 2. FIGS. 5A-5C show the results of treated Southern yellow pine samples after exterior exposure for 2,750 hours, in accordance with various embodiments. As expected, after 2,750 hours of exterior exposure, the first evidence of mold growth was seen on the samples that did not include a hydrophobic film-forming agent (Treatment A, FIG. 5B).

Figure 6A:
FIGS. 6A-6D show the results of scribed coated Southern yellow pine samples after exterior exposure for 3,750 hours, in accordance with various embodiments.

Comparatively, at the same time point, no mold was observed on the sample that included a hydrophobic film-forming agent in the treatment formulation (Treatment B, FIG. 5C), while the untreated wood substrate exhibited significant mold growth across the entire surface (Control, FIG. 5A).

at the site of damage where the protective barrier provided by the acrylic coating had been compromised and the underlying wood substrate was exposed to the environment. Over time however, as can be seen in FIG. 6A, the mold growth expanded beyond the initial area of damage to other parts of the coated substrate. This pattern of mold growth highlights the importance of replenishing biocidal activity at the site of damage after a coating has been damaged to prevent the spread of mold to other parts of the substrate.

Figure 6B:
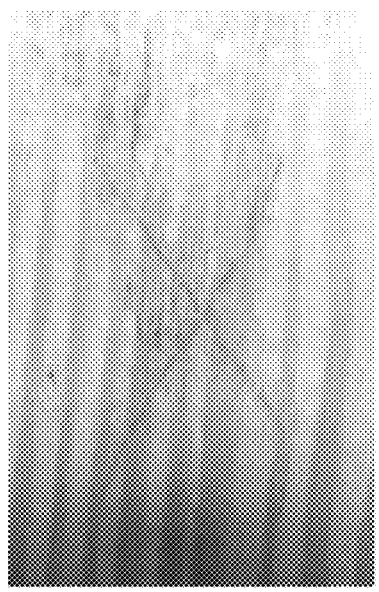
Figure 6C:

FIGS. 6B and 6C illustrate the benefits of restoring a protective barrier at the site of damage after a coating has been damaged. Damaging the coating on the substrate by scribing resulted in the rupturing of the microcapsules present in the area of damage. The release of a hydrophobic film-forming agent into the damage site resulted in the restoration of the coating's barrier properties at the site of damage. The restoration of barrier properties extended the protection of the underlying substrate from mold growth as significantly less mold growth was observed in the site of damage for samples coated with a coating formulation containing a microencapsulated film-forming solution (Comparative Examples B and C). The best control of mold growth was exhibited by the substrates treated with the "Example D" coating formulation. The capsules in this formulation contained a hydrophobic film-forming agent as well as 2 wt % of the hydrophobic biocidal agent, DCOIT.

TABLE 2

| Substrate Treatment | Solvent Blend | Hydrophobic Film-Forming Agent | Hydrophobic Biocidal Agent | Representative Image |
|---|---|---|---|---|
| Control (no treatment) | None | None | None | FIG. 5A |
| Treatment A | Hexyl acetate, ethyl phenyl acetate (99.8 wt %) | None | DCOIT (0.2 wt %) | FIG. 5B |
| Treatment B | Hexyl acetate, ethyl phenyl acetate (39.8 wt %) | Functionalized alkyd resin (60 wt %) | DCOIT (0.2 wt %) | FIG. 5C |

Having demonstrated the importance of incorporating a hydrophobic film-forming agent into the biocidal formulation for longer-term biocidal efficacy, an evaluation of microencapsulated formulations was performed. For these experiments, microcapsules prepared as described in Example 1 above were incorporated into an acrylic wood coating by mixing a wet cake version of the microcapsules (the wet cake referred to here contains roughly 50 wt % capsules and 50 wt % water) into the coating formulation using a mechanical stirrer. The resulting coating formulation was applied using a paintbrush. After allowing the coating to dry for 24 hours, the samples were scribed in an "x" pattern using a 186-micron scribe tool and left at room temperature for 24 hours prior to exposure to either an exterior or interior testing environment. The samples exposed to both environments were sprayed down weekly with water to keep them moist and to simulate the action of rain or other sources of water on the samples. The samples were evaluated periodically and digital images were captured to document the growth of mold on the samples. The results are summarized in Table 3.

FIGS. 6A-6D show the results of scribed coated Southern yellow pine samples after exterior exposure for 3,750 hours, in accordance with various embodiments. Evaluation of the coated wood substrates after 3750 hours of exterior exposure showed that in the case of the control, mold growth started When the coating on substrates coated with the coating formulation described in "Example D" was damaged, the microcapsules incorporated were damaged, releasing a formulation into the site of damage that contained a hydrophobic film-forming agent as well as a hydrophobic biocidagent such that, upon release and solidification, the hydrophobic film-forming agent in the site of damage contained a hydrophobic biocidal agent, affording much longer-lasting control of mold growth.

Figure 6D:
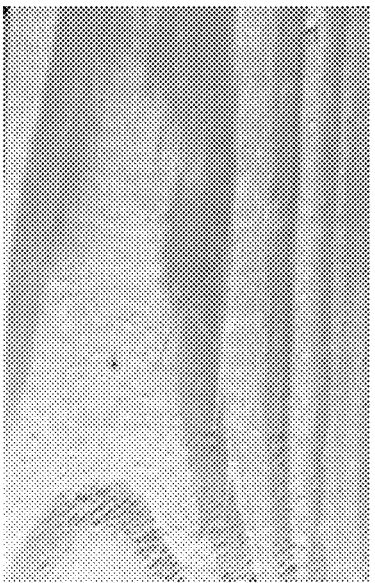

As shown in FIG. 6D, after 3750 hours of exterior exposure, no mold growth was evident in the site of damage. In a more controlled interior environment, mold growth was much slower, but similar results were obtained. After 7000 hours of exposure to an interior high humidity environment, wood samples coated with the "Comparative Example A" formulation exhibited mold growth that initiated at the damage site and eventually spread to more parts of the underlying wood substrate.

Figure 7A:
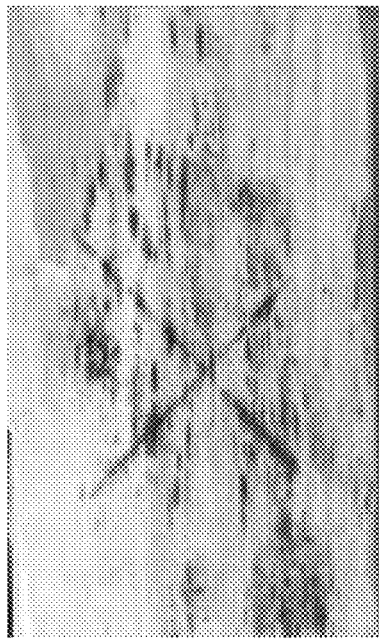
FIGS. 7A and 7B show the results of scribed coated Southern yellow pine samples after exposure to an interior moist environment for 7,000 hours, in accordance with various embodiments.
Figure 7B:

FIGS. 7A and 7B show the results of scribed coated Southern yellow pine samples after interior exposure for 7,000 hours, in accordance with various embodiments. As shown in FIGS. 7A and 7B, samples coated with the "Example D" formulation did not exhibit any mold growth at the site of damage or anywhere else on the sample. Mold growth was shown to originate from the scribed area, but spread to other areas of the substrate in samples coated with the formulation "Comparative Example A," (FIG. 7A) but not in samples coated with the formulation "Example D" (FIG. 7B).

TABLE 3

| Substrate Treatment | Matrix | Microcapsule Core Evaluated | | | Capsule Loading | Representative Image |
|---|---|---|---|---|---|---|
| | | Solvent Blend | Binder | Biocide | | |
| Comparative Example A | Acrylic Coating | — | — | — | — | FIG. 6A |
| Comparative Example B | Acrylic Coating | Xylenes, hexyl acetate, ethyl phenyl acetate (40 wt %) | Functionalized alkyd resin (60 wt %) | — | 5 wt % | FIG. 6B |
| Comparative Example C | Acrylic Coating | Xylenes, ethyl phenyl acetate (40 wt %) | Functionalized alkyd resin (60 wt %) | — | 5 wt % | FIG. 6C |
| Example D | Acrylic Coating | Xylenes, hexyl acetate, ethyl phenyl acetate (38 wt %) | Functionalized alkyd resin (60 wt %) | DCOIT (2 wt %) | 5 wt % | FIG. 6D |

Thus, in various embodiments, the incorporation of the microcapsules disclosed herein into coating formulations applied on wood substrates significantly improved the ability of these coatings to maintain biocidal activity and prevent the growth of biomatter after the coating was damaged. Exterior structures such as wooden decks, fences, playsets etc. that experience scratches, cracking, impact and damage via other types of mechanisms would all benefit from coatings incorporating the microcapsules disclosed here. However, one of ordinary skill in the art will appreciate that all protective materials, whether they are coatings, sealants or adhesives and whether they protect wood, concrete or metal substrates could all benefit from the approach to maintaining long term biocidal activity as disclosed here.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A biocidal formulation, comprising:
 a first microcapsule, comprising:
  a hydrophobic film-forming agent; and
  a hydrophobic biocidal agent; wherein upon rupture of the first microcapsule, the hydrophobic film-forming agent forms a polymerized film comprising the hydrophobic biocidal agent.

2. The biocidal formulation of claim 1, wherein the formulation further comprises a second microcapsule, wherein the second microcapsule comprises a curing agent, and wherein upon rupture of the first and second microcapsules, the curing agent causes the hydrophobic film-forming agent to form a polymerized film comprising the hydrophobic biocidal agent.

3. The biocidal formulation of claim 1, wherein the hydrophobic biocidal agent is miscible with hydrophobic non-polar and/or polar aprotic solvents.

4. The biocidal formulation of claim 3, wherein the hydrophobic biocidal agent comprises an isothiazolinone.

5. The biocidal formulation of claim 4, wherein the hydrophobic biocidal agent comprises 4,5-dichloro-2-n-octyl-4-isothiazolin-3-one (DCOIT) and/or benzisothiazolin-3-one (BIT).

6. The biocidal formulation of claim 1, wherein the hydrophobic film-forming agent comprises a thermoplastic polymer, a monomer, or a resin.

7. The biocidal formulation of claim 6, wherein the resin comprises an alkyd, an epoxy, a siloxane, a silane, a polyester, a vinyl ester, an isocyanate, a polyacrylate, a polyurethane, a polyurea resin, and/or an acrylate.

8. The biocidal formulation of claim 1, wherein the first microcapsule comprises a shell wall comrising poly(oxymethylene urea), poly(oxymethylene melamine), polyurethane, polyurea, polyacrylate, gelatin, polydimethylsiloxane, a thermoplastic polymer, a thermoplastic monomer, or a resin.

9. The biocidal formulation of claim 8, wherein the resin comprises an alkyd, an epoxy, a siloxane, a silane, a polyester, a vinyl ester, a silicone, an isocyanate, a polyacrylate, a polyurethane, a polyurea resin, and/or an acrylate.

10. The biocidal formulation of claim 1, wherein the hydrophobic film-forming agent comprises a functionalized alkyd resin, poly(methyl methacrylate) (PMMA), a silicone epoxy functionalized alkyd, or an epoxy resin.

11. The biocidal formulation of claim 10, wherein the hydrophobic film-forming agent comprises 4,5-dichloro-2-n-octyl-4-isothiazolin-3-one (DCOIT) and/or benzisothiazolin-3-one (BIT).

12. The biocidal formulation of claim 11, wherein the first microcapsule further comprises a xylene, hexyl acetate, and/or ethyl phenyl acetate.

13. The biocidal formulation of claim 12, wherein the first microcapsule comprises xylene, hexyl acetate, and ethyl phenyl acetate; wherein the hydrophobic film-forming agent comprises a functionalized alkyd resin; and wherien the hydrophobic film-forming agent comprises 4,5-dichloro-2-n-octyl-4-isothiazolin-3-one (DCOIT).

14. The biocidal formulation of claim 1, wherein the first microcapsule comprises a core material that is at least 60% of a total mass of the first microcapsule; wherein a thickness of a shell wall of the first microcapsule is 2 microns or less; and wherein a contribution of the thickness of the shell wall to a diameter of the microcapsule is no more than about 20%.

15. A protective material comprising:
 a polymeric material matrix; and
 a first microcapsule, wherein the first microcapsule comprises:

a hydrophobic film-forming agent; and
a hydrophobic biocidal agent; wherein upon rupture of the first microcapsule, the hydrophobic film-forming agent forms a polymerized film comprising the hydrophobic biocidal agent.

16. The protective material of claim 15, wherein the polymeric material matrix further comprises a second microcapsule, wherein the second microcapsule comprises a curing agent, and wherein upon rupture of the first and second microcapsules, the curing agent causes the hydrophobic film-forming agent to form a polymerized film comprising the hydrophobic biocidal agent.

17. The protective material of claim 15, wherein the polymeric material matrix comprises a coating, stain, sealant, or adhesive.

18. The protective material of claim 17, wherein the polymeric material matrix comprises a polymer-based coating, stain, sealant, or adhesive.

19. The protective material of claim 18, wherein the polymeric material matrix comprises an acrylic an epoxy, a polyurethane, a polyurea, a polyester, or a siloxane.

20. The protective material of claim 15, wherein the hydrophobic biocidal agent is miscible with hydrophobic non-polar and/or polar aprotic solvents.

21. The protective material of claim 20, wherein the hydrophobic biocidal agent comprises an isothiazolinone.

22. The protective material of claim 21, wherein the hydrophobic biocidal agent comprises 4,5-dichloro-2-n-octyl-4-isothiazolin-3-one (DCOIT) and/or benzisothiazolin-3-one (BIT).

23. The protective material of claim 15, wherein the hydrophobic film-forming agent comprises a thermoplastic polymer, a monomer, or a resin.

24. The protective material of claim 23, wherein the resin comprises an alkyd, an epoxy, a siloxane, a silane, a polyester, a vinyl ester, a silicone, an isocyanate, a polyacrylate, a polyurethane, a polyurea resin, and/or an acrylate.

25. The protective material of claim 15, wherein the first microcapsule comprises a shell wall comprising poly(oxymethylene urea), poly(oxymethylene melamine), polyurethane, polyurea, polyacrylate, gelatin, polydimethylsiloxane, a thermoplastic polymer, a thermoplastic monomer, or a resin.

26. The protective material of claim 25, wherein the resin comprises an alkyd, an epoxy, a siloxane, a silane, a polyester, a vinyl ester, a silicone, an isocyanate, a polyacrylate, a polyurethane, a polyurea resin, and/or an acrylate.

27. The protective material of claim 15, wherein the hydrophobic film-forming agent comprises a functionalized alkyd resin, poly(methyl methacrylate) (PMMA), a silicone epoxy functionalized alkyd, or an epoxy resin.

28. The protective material of claim 27, wherein the hydrophobic film-forming agent comprises 4,5-dichloro-2-n-octyl-4-isothiazolin-3-one (DCOIT) and/or benzisothiazolin-3-one (BIT).

29. The protective material of claim 28, wherein the first microcapsule further comprises a xylene, hexyl acetate, and/or ethyl phenyl acetate.

30. The protective material of claim 29, wherein the first microcapsule comprises xylene, hexyl acetate, and ethyl phenyl acetate; wherein the hydrophobic film-forming agent comprises a functionalized alkyd resin; and wherein the hydrophobic film-forming agent comprises 4,5-dichloro-2-n-octyl-4-isothiazolin-3-one (DCOIT).

31. The protective material of claim 15, wherein the first microcapsule comprises a core material that is at least 60% of a total mass of the first microcapsule; wherein a thickness of a shell wall of the first microcapsule is 2 microns or less; and wherein a contribution of the thickness of the shell wall to a diameter of the microcapsule is no more than about 20%.

32. A method of increasing a biocidal activity of a protective material, comprising:
providing a protective material; and
adding the biocidal formulation of claim 1 to the protective material, thereby increasing the biocidal activity of the protective material.

33. The method of claim 32, wherein the protective material is a coating, stain, sealant, or adhesive.

34. A method of increasing a biocidal activity of a porous substrate, comprising:
providing a protective material comprising the biocidal formulation of claim 1; and
applying the material to the porous substrate.

* * * * *